United States Patent
Bille

(10) Patent No.: US 6,428,533 B1
(45) Date of Patent: Aug. 6, 2002

(54) CLOSED LOOP CONTROL FOR REFRACTIVE LASER SURGERY (LASIK)

(75) Inventor: Josef Bille, Heidelberg (DE)

(73) Assignee: 20/10 Perfect Vision Optische Geraete GmbH, Heidelberg (DE)

(*) Notice: Subject to any disclaimer, the term of this patent is extended or adjusted under 35 U.S.C. 154(b) by 119 days.

(21) Appl. No.: 09/690,774

(22) Filed: Oct. 17, 2000

(51) Int. Cl.[7] .................................................. A61B 18/18
(52) U.S. Cl. ............................................. 606/11; 606/4
(58) Field of Search ............................. 606/4, 5, 6, 10, 606/11, 12

(56) References Cited

U.S. PATENT DOCUMENTS

| | | |
|---|---|---|
| 4,579,430 A | 4/1986 | Bille |
| 4,772,115 A | 9/1988 | Gersten |
| 4,887,592 A | 12/1989 | Loertscher |
| 4,988,348 A | 1/1991 | Bille |
| 5,062,702 A | 11/1991 | Bille |
| 6,050,687 A | 4/2000 | Bille |
| 6,095,651 A | * 8/2000 | Williams et al. ............ 351/246 |

* cited by examiner

Primary Examiner—Edward K. Look
Assistant Examiner—Michael Leslie
(74) Attorney, Agent, or Firm—Nydegger & Associates

(57) ABSTRACT

A closed-loop control system for the superficial photoablation of stromal tissue from an exposed surface includes an active mirror for directing a diagnostic laser beam through the exposed surface to a focal point on the retina of an eye. The reflected beam is analyzed by a detector to identify a distorted wavefront that is indicative of required corrections, and an induced wavefront that is indicative of optical aberrations that have been mechanically introduced when the stromal tissue was exposed. A compensator alters a desired wavefront with the induced wavefront to create a rectified wavefront. A comparator then compares the rectified wavefront with the distorted wavefront to create an error signal. In the operation of the closed-loop control system, the error signal is used to maintain a focal point on the retina for the diagnostic laser beam. Also, at a null, the error signal indicates when the required amount of stromal tissue has been photoablated.

19 Claims, 1 Drawing Sheet

CLOSED LOOP CONTROL FOR REFRACTIVE LASER SURGERY (LASIK)

FIELD OF THE INVENTION

The present invention pertains generally to the control of a laser beam. More particularly, the present invention pertains to systems and methods for controlling a laser beam by using an active mirror in accordance with wavefront analysis techniques. The present invention is particularly, but not exclusively, useful as a system and method for controlling a laser beam in ophthalmic applications wherein mechanically introduced optical aberrations require compensation.

BACKGROUND OF THE INVENTION

In preparation for a so-called "flap and zap" (Lasik) ophthalmic laser surgery procedure, it is common practice to first create a stromal flap. Typically, this is done by mechanically cutting into the stroma to create the flap. To date, it has been the practice to accept the resultant incision as being substantially flat. Actually, however, the interface surface that results when the flap is created is not flat. Instead, due to irregularities in the sharpness of the cutting blade, due to imperfect aplanation for stabilizing the cornea during cutting of the flap, and due to the resistance between the stromal tissue and the cutting blade as the flap is created, the resulting incision typically includes several surface irregularities. These irregularities, unfortunately, are significant. Indeed, it happens that these irregularities are generally in the form of asymmetric undulations that may vary in amplitude by as much as ten microns, and extend over a distance of as much as a millimeter. As is well known, undulations (surface irregularities) of this magnitude will induce noticeable aberrations in any wavefront that passes through the surface.

It is known that an excimer laser has a relatively large spot size (e.g. approximately one millimeter in diameter). It is also known that an excimer laser will superficially photoablate an exposed layer of stromal tissue to a substantially uniform depth within the spot size. Consequently, any undulations of one millimeter that are initially present on an exposed surface of stromal tissue will persist and will still be present after the procedure has been completed. This, however, is good. Although the surface undulations will introduce aberrations during the procedure, these same aberrations will be cancelled when the flap is lowered onto the exposed surface.

Heretofore, whenever closed-loop control of an excimer laser has been employed during ophthalmic surgery, the contribution of the surface irregularities (undulations) to the total aberrations of the eye has been generally disregarded. Consequently, it has been the practice in earlier closed-loop control systems to generate a controlling error signal by comparing the extent of actual tissue photoablation to the predetermined amount of desired photoablation. Using wavefront analysis, this has been done. by identifying the actual distorted wavefront that is created by the stromal tissue (including the undulation contribution), and then comparing the distorted wavefront with a desired wavefront to generate the error signal. The desired wavefront, however, is normally determined off-site and is the result of a diagnostic examination. Thus, it is predetermined, and does not account for aberrations that are subsequently introduced by surface undulations (irregularities) when the flap is subsequently created at the time the procedure is to be performed. The result here is that the undulations on the exposed surface are removed along with the desired tissue removal.

In light of the above, it is an object of the present invention to provide a system and method for superficial photoablation of stromal tissue which compensates for the induced aberrations that are introduced when a flap of the cornea is mechanically created. It is another object of the present invention to provide a system and method for superficial photoablation of stromal tissue which generates an error signal that allows for more precise closed-loop control of photoablation during a procedure. Yet another object of the present invention is to provide a system and method for superficial photoablation of stromal tissue which is relatively easy to use, is simple to implement and is comparatively cost effective.

SUMMARY OF THE PREFERRED EMBODIMENTS

In accordance with the present invention, a closed-loop control system is provided for use in a so-called LASIK "flap and zap" procedure. Specifically, this closed-loop control is accomplished using wavefront analysis, and it is provided to compensate for optical aberrations that can be mechanically induced during the procedure. In the context of the present invention, it is important to appreciate that the patient will be examined and diagnosed prior to the corrective surgical procedure. Thus, the naturally occurring optical aberrations of an eye, that are unwanted and therefore need to be corrected, will be known and can serve as a starting point.

Importantly, the naturally occurring optical aberrations of an eye can be characterized as a distorted wavefront. As a corrective procedure is conducted, however, tissue will be removed from the stroma and the distorted wavefront will change accordingly. Deviations between the dynamically changing, distorted wavefront and a predetermined, desired wavefront (e.g. a plane wavefront) will then indicate the extent of corrections that are still required by the procedure. As appreciated by the present invention, in addition to all of this, there is a need to compensate for mechanically introduced optical aberrations.

In detail, the closed-loop control system of the present invention includes a source for generating an incising laser beam. Preferably, the incising laser beam is an excimer laser and will have a focal spot that is approximately one millimeter in diameter. As intended for the present invention, and implied above, the incising laser beam is only used to photoablate tissue from the exposed stromal surface after the flap has been lifted.

In addition to the incising laser source, the system of the present invention also includes an additional laser source for generating a diagnostic laser beam. Further, there is a deformable mirror for directing this diagnostic laser beam through the exposed stromal surface toward a focal spot on the retina of the eye. Preferably, the deformable mirror that is used for the present invention is of a type disclosed in U.S. application Ser. No. 09/512,440 which issued to Bille et al. for an invention entitled "Method for Programming an Active Mirror to Mimic a Wavefront" and which is assigned to the same assignee as the present invention. Light in the diagnostic laser beam will then be reflected from the focal spot on the retina and directed back through the exposed stromal surface.

A detector is positioned to receive light of the diagnostic beam that is reflected from the retina, back through the exposed stromal surface. At this point, it is to be appreciated that light in the diagnostic beam that is reflected from the retina will include two identifiable components. One component is a contribution that is characteristic of the distorted wavefront that was determined earlier during patient diagnosis. The other component will be a contribution from the optical aberrations that are introduced during the cutting of the corneal flap. Importantly, both component contributions can be characterized by distinct wavefronts.

For purposes of the present invention, the component contribution that is introduced during the cutting of the corneal flap is hereinafter referred to as an induced wavefront. On the other hand, the distorted wavefront has been previously determined during diagnosis. Therefore, the induced wavefront, which will not change during the procedure, can be determined by removing the distorted wavefront from the actually detected wavefront. Thus, the detector identifies and models, or generates, the induced wavefront that has characteristics of the mechanically induced optical aberrations. All of this is done using actual real-time characteristics of the cornea.

The system of the present invention also incorporates a compensator. Specifically, the compensator uses the induced wavefront to alter the desired wavefront. This is done by incorporating the induced wavefront with the desired wavefront, to create a rectified wavefront. In most applications, the desired wavefront will be a simple plane wavefront.

At this point it is helpful to recall that the system of the present invention is concerned with four specifically different wavefronts. These are: 1) a distorted wavefront that is characteristic of the uncorrected eye; 2) a desired wavefront for the corrected eye (this is the overall objective of the procedure); 3) an induced wavefront that is characteristic of the optical aberrations introduced during creation of the flap; and 4) a rectified wavefront that is a summation of 2) and 3).

In accordance with well known techniques for establishing closed-loop control, it is necessary to create an error signal. For the present invention, this function is accomplished by a comparator that compares the rectified wavefront (i.e. the desired wavefront incorporating the induced wavefront) with the distorted wavefront. Stated differently, the error signal represents the amount of correction required in the cornea (desired wavefront), and it includes a factor that compensates for the optical aberrations that were mechanically introduced during creation of the flap (induced wavefront). In effect, during the procedure the induced wavefront is preserved.

For the system of the present invention, the error signal is actually used for two purposes. For one, the error signal is used to reconfigure the deformable mirror and to thereby maintain a focal spot on the retina. This is important in order for the system to continuously determine the distorted wavefront as it is being altered by the photoablation of stromal tissue. For another, the error signal is used to deactivate the incising laser when the error signal is a null to thereby indicate that the proper correction has been accomplished.

Once the procedure has been completed, the flap is lowered onto the exposed, and now altered, stromal surface. Because the induced wavefront was preserved during the procedure, the undulations on the flap will mate with the preserved undulations on the exposed stromal surface. This will effectively cancel the optical aberrations that would otherwise be present.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
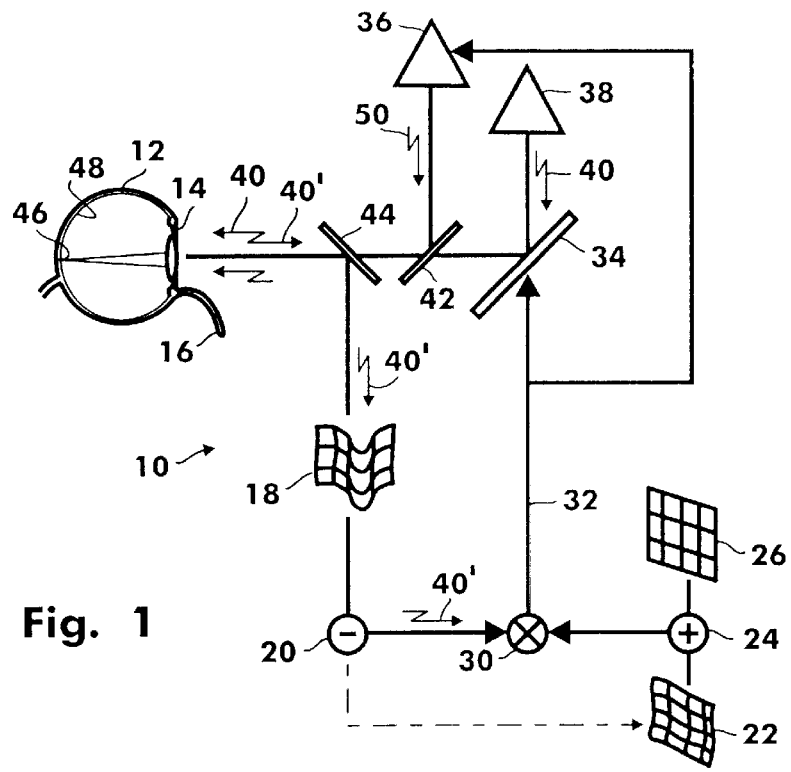
FIG. 1 is a schematic layout showing the interrelationships of components in a system for controlling the superficial photoablation of tissue from an exposed stromal surface of an eye in accordance with the present invention.

Referring initially to FIG. 1 a system for controlling the superficial photoablation of tissue from an exposed stromal surface of an eye is shown and generally designated 10. In accordance with the present invention, the purpose of the system 10 is to control the photoablation of tissue from the eye 12. More specifically, the purpose of the system 10 is to control the photoablation of tissue from the surface 14 of stromal tissue that is exposed when a flap 16 of corneal tissue is lifted from the surface 14. As contemplated for the present invention, the flap 16 will be mechanically created using a sharp cutting instrument such as a keratome (not shown).

Figure 2:
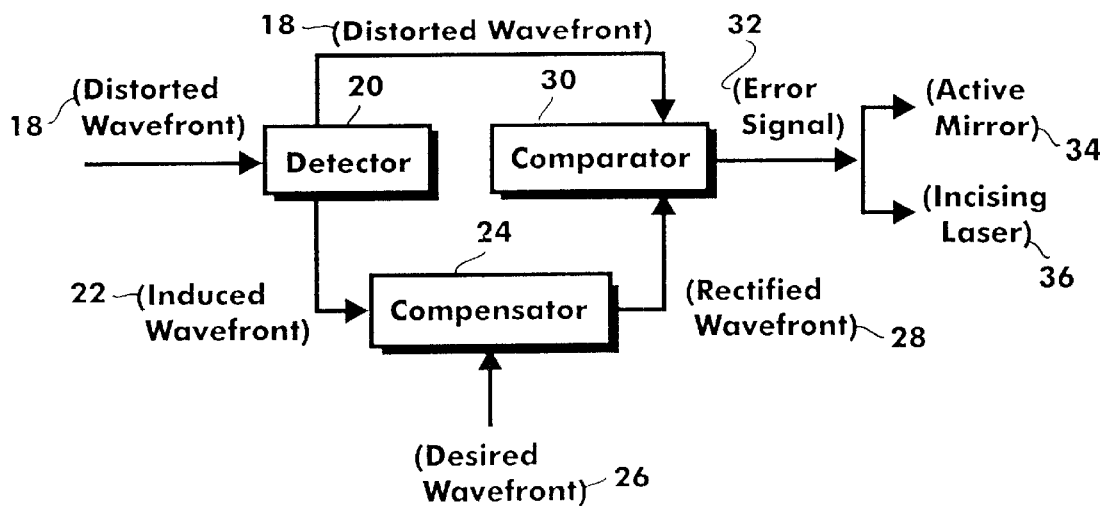
FIG. 2 is a functional representation of the wavefront analysis techniques used in the operation of the system of the present invention.

An overview of the system 10 from the perspective of wavefront analysis techniques is perhaps best appreciated with reference to FIG. 2. In FIG. 2 it will be seen that initially a distorted wavefront 18 is received by a detector 20. As a general proposition it will be understood that the distorted wavefront 18 may come from any source. In the context of the present invention, however, the distorted wavefront 18 is received from the eye 12. This distorted wavefront 18 is then processed and analyzed by the detector 20.

For the system 10, the detector 20 preferably includes a Hartmann-Shack type sensor which is capable of generating data that will be representative of the distorted wavefront 18. As contemplated for the system 10, the distorted wavefront 18 that is received from the eye 12 will include two components of information. One component is caused by the naturally occurring optical aberrations in the eye 12 that are to be corrected. The other component includes the optical aberrations that were mechanically induced when the flap 16 was being created by a cutting instrument (e.g. keratome). Using predetermined diagnostic information about the corrections to the eye 12 that are to be made by the system 10, the detector 20 determines an induced wavefront 22 that is representative of the optical aberrations induced by cutting the flap 16. Like the distorted wavefront 18, the induced wavefront 22 is characterized by useable data.

Once an induced wavefront 22 has been determined by the detector 20, the data for the induced wavefront 22 is transferred to a compensator 24. At the compensator 24 the induced wavefront 22 is incorporated with a desired wavefront 26 to create a rectified wavefront 28. As a general notion, the desired wavefront 26 will have the optical characteristics that are desired for the eye 12 after the procedure has been completed. Thus, the desired wavefront 26 will, in most instances, be a plane wavefront.

A comparator 30 is used for the system 10 to determine the differences that exist between the distorted wavefront 18 and the rectified wavefront 28. Thus, the function of the comparator 30 is, essentially, to generate an error signal 32. As indicated in FIG. 2, the use of the error signal 32 is at least two-fold. For one, the error signal 32 is used to program an active mirror 34. For another, the error signal 32 is used to control the operation of an incising laser source 36. As contemplated by the present invention, the incising laser source 36 will be an excimer laser. The interaction of these functions will be best appreciated by referring back to FIG. 1.

In FIG. 1 it will be seen that the system 10 includes a diagnostic laser source 38 which is used to generate a diagnostic laser beam 40. As shown, this diagnostic laser beam 40 is directed toward the active mirror 34 for reflection therefrom. As indicated above, the active mirror 34 used in the system 10 is preferably of a type disclosed in U.S. application Ser. No. 09/512,440 which issue to Bille et al. for an invention entitled "Method for Programming an Active Mirror to Mimic a Wavefront" and which is assigned to the same assignee as the present invention. After being reflected from the active mirror 34, the diagnostic laser beam 40 passes through a beam splitter 42 and a beam splitter 44 enroute to the eye 12.

Using appropriate optical elements (not shown) the diagnostic laser beam 40 is focused to a focal spot 46 on the retina 48 of the eye 12. The reflected diagnostic laser beam 40' then passes out of the eye 12 through the exposed stromal surface 14 and is directed by the beam splitter 44 (which is acting like a turning mirror) toward the detector 20. In line with the above disclosure, the diagnostic laser beam 40' is characterized by the distorted wavefront 18. As indicated above, the detector 20 is then used to extract the induced wavefront 22 from the distorted wavefront 18. The induced wavefront 22 is then sent to the compensator 24 and the distorted wavefront 18 is sent to the comparator 30. The rectified wavefront 28 (i.e. a combination of desired wavefront 26 and induced wavefront 22) is then compared with the distorted wavefront 18 by the comparator 30 to generate the error signal 32.

FIG. 1 shows that the error signal 32 is sent both to the active mirror 34 and to the incising laser source 36 (e.g. an excimer laser). As intended for the system 10 of the present invention, the incising laser source 36 is activated by the error signal 32 to generate an incising laser beam 50 which will be used to photoablate tissue from the exposed stromal surface 14 of the eye 12. Specifically, as shown, the incising laser beam will be directed by the beam splitter 42 (acting like a turning mirror) toward the surface 14 of the eye 12. As tissue is photoablated from the surface 14, the optical characteristics of the eye 12 will be changed. Consequently, the distorted wavefront 18 of the reflected diagnostic beam 40' and the focal spot 46 on the retina 48 will also be changed. The error signal 32, however, can maintain the focal spot 46 on the retina 48 by properly programming the active mirror 34. Accordingly, the incising laser source 36 will remain activated until the error signal 32 is a null. When the error signal 32 is a null, the corrective procedure has been completed and the entire system 10 can be shut down.

While the particular Closed Loop Control for Refractive Laser Surgery (Lasik) as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A closed-loop control system for superficial photoablation of tissue from an exposed stromal surface of an eye wherein the exposed surface introduces mechanically induced optical aberrations, said system comprising:

a source for generating an incising laser beam to photoablate tissue from the exposed surface;

a source for generating a diagnostic laser beam;

a deformable mirror for directing said diagnostic laser beam through the exposed stromal surface to a focal spot on the retina of the eye;

a detector for using light from said diagnostic beam reflected from the retina through the exposed stromal surface to generate an induced wavefront having characteristics of the mechanically induced optical aberrations, together with a distorted wavefront having actual real-time characteristics of the cornea;

a compensator for altering a predetermined desired wavefront by incorporating said induced wavefront therewith to create a rectified wavefront;

a comparator for comparing said rectified wavefront with said distorted wavefront to create an error signal;

a means for reconfiguring said deformable mirror in accordance with said error signal to maintain said focal spot on the retina; and a means for ceasing generation of said incising laser beam when said error signal is a null.

2. A system as recited in claim 1 wherein said source for generating said incising laser beam is an excimer laser.

3. A system as recited in claim 1 wherein said detector for modeling the distorted wavefront is a Hartmann-Shack sensor unit.

4. A system as recited in claim 1 wherein the stromal surface is exposed using a blade to create a stromal flap, the stromal flap being movable to expose the surface for photoablation of tissue.

5. A system as recited in claim 1 wherein the desired wavefront is a plane wavefront.

6. A method for controlling the superficial photoablation of tissue from an exposed stromal surface of an eye wherein the exposed surface introduces mechanically induced optical aberrations, said method comprising the steps of:

predetermining a desired wavefront for the eye;

generating a diagnostic laser beam;

using said diagnostic laser beam to identify an induced wavefront, said induced wavefront being characteristic of the mechanically induced optical aberrations;

altering said desired wavefront with said induced wavefront to create a rectified wavefront;

generating an incising laser beam to photoablate tissue from the exposed surface;

using a deformable mirror to direct said diagnostic laser beam through the exposed stromal surface to a focal spot on the retina of the eye;

detecting a distorted wavefront with light from said diagnostic beam reflected from the retina through the exposed stromal surface, said distorted wavefront having actual real-time characteristics of the cornea;

comparing said rectified wavefront with said distorted wavefront to create an error signal;

reconfiguring said deformable mirror in accordance with said error signal to maintain said focal spot on the retina; and ceasing generation of said incising laser beam when said error signal is a null.

7. A method as recited in claim 6 wherein said step for generating said incising laser beam is accomplished using an excimer laser.

8. A method as recited in claim 6 wherein said step for identifying the induced wavefront is accomplish using a Hartmann-Shack sensor unit.

9. A method as recited in claim 6 wherein the stromal surface is exposed using a blade to create a stromal flap, the stromal flap being movable to expose the surface for photoablation of tissue.

10. A method as recited in claim 6 wherein the desired wavefront is a plane wavefront.

11. A method for controlling the superficial photoablation of tissue from an exposed stromal surface of an eye comprising the steps of:

detecting a distorted wavefront in the light of a diagnostic laser beam after reflection of said diagnostic laser beam from a focal spot on the retina of the eye;

extracting an induced wavefront from said distorted wavefront;

adding said induced wavefront to a desired wavefront to obtain a rectified wavefront;

comparing said rectified wavefront with said distorted wavefront to generate an error signal;

employing said error signal to control said focal spot of said diagnostic beam on the retina for subsequent reuse in said detecting step; and monitoring said error signal as said distorted wavefront changes during photoablation of exposed stromal tissue to cease photoablation thereof when said error signal is at a null.

12. A method as recited in claim 11 wherein said distorted wavefront includes optical characteristics of the uncorrected eye.

13. A method as recited in claim 12 wherein said desired wavefront is a plane wavefront.

14. A method as recited in claim 13 wherein the exposed surface introduces mechanically induced optical aberrations and said induced wavefront is characteristic of the mechanically induced optical aberrations.

15. A method as recited in claim 14 wherein said employing step comprises the steps of:

using a deformable mirror to direct said diagnostic laser beam through the exposed stromal surface to said focal spot on the retina of the eye; and reconfiguring said deformable mirror in accordance with said error signal to maintain said focal spot on the retina.

16. A method as recited in claim 11 wherein said photoablation is accomplished using an excimer laser.

17. A method as recited in claim 11 wherein said extracting step is accomplished using a Hartmann-Shack sensor unit.

18. A method as recited in claim 11 wherein the stromal surface is exposed using a blade to create a stromal flap, the stromal flap being movable to expose the surface for photoablation of tissue.

19. A method as recited in claim 18 wherein said blade is a microkeratome.

* * * * *